US011763815B2

(12) United States Patent
Judy et al.

(10) Patent No.: US 11,763,815 B2
(45) Date of Patent: Sep. 19, 2023

(54) VOICE RECOGNITION FOR PATIENT CARE ENVIRONMENT

(71) Applicant: Hill-Rom Services, Inc., Batesville, IN (US)

(72) Inventors: Jerald W. Judy, Raleigh, NC (US); Bita Akhlaghi, Cary, NC (US); David O. Melgar, Raleigh, NC (US); Daniel Sampson, Morrisville, NC (US); Edwin N. Swift, Apex, NC (US); Jennifer A. Gunn, Durham, NC (US); Darren S. Hudgins, Cary, NC (US); Patrick D. Harrison, St. Johns, FL (US); William B. Richard, Jamestown, RI (US)

(73) Assignee: Hill-Rom Services, Inc., Batesville, IN (US)

( * ) Notice: Subject to any disclaimer, the term of this patent is extended or adjusted under 35 U.S.C. 154(b) by 203 days.

(21) Appl. No.: 17/355,416

(22) Filed: Jun. 23, 2021

(65) Prior Publication Data

US 2021/0319793 A1    Oct. 14, 2021

Related U.S. Application Data

(63) Continuation of application No. 16/437,064, filed on Jun. 11, 2019, now Pat. No. 11,062,707.
(Continued)

(51) Int. Cl.
*G10L 15/22* (2006.01)
*G16H 80/00* (2018.01)
*A61B 5/00* (2006.01)

(52) U.S. Cl.
CPC ............ *G10L 15/22* (2013.01); *A61B 5/0002* (2013.01); *G16H 80/00* (2018.01); *G10L 2015/223* (2013.01)

(58) Field of Classification Search
CPC ...... A61B 5/0002; A61B 5/1113; A61B 34/25; A61B 6/467; A61B 6/502; A61G 7/0527;
(Continued)

(56) References Cited

U.S. PATENT DOCUMENTS 5,668,928 A    9/1997 Groner
5,781,442 A    7/1998 Engelson et al.
(Continued)

FOREIGN PATENT DOCUMENTS

WO    2019/179888 A1    9/2019

OTHER PUBLICATIONS

"Voice Recognition Based Advance Patient's Room Automation," by Tijaswiny Singh et al.; International Journal of Research in Engineering and Technology, vol. 4, Issue 6; Jun. 2015; pp. 308-310 (3 pages).
(Continued)

*Primary Examiner* — Gerald Gauthier
(74) *Attorney, Agent, or Firm* — Barnes & Thornburg LLP

(57) ABSTRACT

A location monitoring system tracks a location of a user within a healthcare facility. When the user is detected in a patient room an electronic controller activates a voice command database having a plurality of voice commands specific to the user. A microphone located in the patient room receives one of the plurality of voice commands. The electronic controller transmits the one of the plurality of voice commands to a remote device positioned outside of the patient room.

16 Claims, 5 Drawing Sheets

Related U.S. Application Data

(60) Provisional application No. 62/691,018, filed on Jun. 28, 2018.

(58) Field of Classification Search
CPC .... A61G 7/012; G08B 25/028; G08B 21/028; G08B 25/009; G10L 15/22; G10L 2015/223; G16H 10/65; G16H 40/20; G16H 40/63; G16H 40/67; G16H 80/00; G16H 10/60; H04L 67/52; H04M 3/4936; A61C 1/0007; A61N 1/37247; G06F 3/167; G06F 16/532
See application file for complete search history.

(56) References Cited

U.S. PATENT DOCUMENTS

| | | | | |
|---|---|---|---|---|
| 5,838,223 | A * | 11/1998 | Gallant | G08B 25/009 340/286.07 |
| 5,970,457 | A * | 10/1999 | Brant | G16H 40/63 704/275 |
| 6,014,626 | A * | 1/2000 | Cohen | G16H 40/67 704/271 |
| 6,216,104 | B1 | 4/2001 | Moshfeghi et al. | |
| 6,353,809 | B2 | 3/2002 | Takahashi et al. | |
| 7,849,400 | B2 | 12/2010 | Ritter et al. | |
| 8,310,179 | B2 | 11/2012 | Clough | |
| 9,230,421 | B2 | 1/2016 | Reeder et al. | |
| 9,236,046 | B2 | 1/2016 | Watson et al. | |
| 10,290,071 | B2 | 5/2019 | Heil et al. | |
| 10,347,255 | B1 | 7/2019 | Paul et al. | |
| 10,417,385 | B2 | 9/2019 | Kusens et al. | |
| 10,474,808 | B2 | 11/2019 | Huster | |
| 10,546,655 | B2 | 1/2020 | Owen et al. | |
| 10,937,543 | B1 | 3/2021 | Newton | |
| 11,062,707 | B2 * | 7/2021 | Judy | G16H 40/63 |
| 11,621,000 | B2 * | 4/2023 | Weeks | G06F 16/532 704/275 |
| 2001/0032085 | A1 * | 10/2001 | Goedeke | A61N 1/37247 704/E15.044 |
| 2003/0033151 | A1 * | 2/2003 | Vozick | A61C 1/0007 704/E15.045 |
| 2003/0182177 | A1 | 9/2003 | Monchi et al. | |
| 2005/0004802 | A1 * | 1/2005 | Johnson | A61B 6/467 704/275 |
| 2005/0021369 | A1 | 1/2005 | Cohen et al. | |
| 2005/0119914 | A1 | 6/2005 | Batch | |
| 2006/0049936 | A1 * | 3/2006 | Collins | G08B 21/028 340/539.11 |
| 2006/0279427 | A1 * | 12/2006 | Becker | G16H 40/20 340/539.13 |
| 2007/0080801 | A1 * | 4/2007 | Weismiller | G01S 5/0226 340/539.13 |
| 2007/0118384 | A1 * | 5/2007 | Gustafson | A61B 6/502 704/E15.045 |
| 2007/0150288 | A1 * | 6/2007 | Wang | G10L 15/22 704/E15.044 |
| 2007/0156456 | A1 | 7/2007 | McGillin et al. | |
| 2008/0077408 | A1 * | 3/2008 | Wang | G10L 15/22 704/E15.044 |
| 2009/0049610 | A1 * | 2/2009 | Heimbrock | A61G 7/012 704/275 |
| 2009/0177477 | A1 * | 7/2009 | Nenov | G16H 10/60 704/E15.04 |
| 2009/0212956 | A1 * | 8/2009 | Schuman | H04L 67/52 340/286.07 |
| 2009/0243833 | A1 * | 10/2009 | Huang | G16H 10/65 340/505 |
| 2010/0036667 | A1 * | 2/2010 | Byford | G16H 40/67 704/E21.001 |
| 2010/0111269 | A1 * | 5/2010 | Younger | H04M 3/4936 379/88.04 |
| 2010/0131280 | A1 * | 5/2010 | Bogineni | G10L 15/22 704/275 |
| 2010/0256983 | A1 | 10/2010 | Perkins et al. | |
| 2010/0286490 | A1 | 11/2010 | Koverzin | |
| 2011/0208541 | A1 * | 8/2011 | Wilson | A61G 7/0527 705/2 |
| 2012/0136667 | A1 | 5/2012 | Emerick et al. | |
| 2012/0212582 | A1 | 8/2012 | Deutsch | |
| 2013/0103419 | A1 | 4/2013 | Beaudry | |
| 2013/0124277 | A1 | 5/2013 | Ellis | |
| 2014/0274152 | A1 | 9/2014 | Lichti | |
| 2015/0106092 | A1 | 4/2015 | Nolte et al. | |
| 2015/0151051 | A1 | 6/2015 | Tsoukalis | |
| 2015/0363563 | A1 | 12/2015 | Hallwachs | |
| 2016/0148489 | A1 * | 5/2016 | Reeder | A61B 5/1113 340/501 |
| 2016/0180045 | A1 | 6/2016 | Syed | |
| 2016/0278652 | A1 | 9/2016 | Kaib et al. | |
| 2017/0005982 | A1 | 1/2017 | Gould et al. | |
| 2017/0221344 | A1 | 8/2017 | Cox et al. | |
| 2018/0018434 | A1 | 1/2018 | Assan et al. | |
| 2018/0168755 | A1 * | 6/2018 | Cagle | A61B 34/25 |
| 2018/0285094 | A1 | 10/2018 | Housel et al. | |
| 2019/0043501 | A1 * | 2/2019 | Ramaci | G16H 40/20 |
| 2019/0244707 | A1 | 8/2019 | Becker et al. | |
| 2019/0272145 | A1 | 9/2019 | Sharma et al. | |
| 2020/0005783 | A1 * | 1/2020 | Judy | G16H 40/63 |
| 2020/0066402 | A1 * | 2/2020 | Bechtel | G16H 40/20 |
| 2020/0121186 | A1 | 4/2020 | Collins, Jr. et al. | |
| 2021/0051223 | A1 | 2/2021 | Hatch et al. | |
| 2021/0319793 | A1 * | 10/2021 | Judy | G16H 80/00 |
| 2023/0123443 | A1 * | 4/2023 | Atarot | G06F 3/167 704/275 |

OTHER PUBLICATIONS

Extended European Search Report for European Patent Application No. 19181030.8; dated Nov. 22, 2019 (7 pages).

* cited by examiner

VOICE RECOGNITION FOR PATIENT CARE ENVIRONMENT

CROSS-REFERENCE TO RELATED APPLICATIONS

This application is a continuation of U.S. application Ser. No. 16/437,064, filed Jun. 11, 2019, which claims the benefit, under 35 U.S.C. § 119(e), of U.S. Provisional Patent Application No. 62/691,018, filed Jun. 28, 2018, each of which is expressly incorporated by reference herein.

BACKGROUND

The present disclosure relates to voice recognition systems used in healthcare facilities to provide attention to patient needs.

Patients in healthcare facilities generally require assistance while in the patient room. Nurse call buttons are typically available to the patient, but are non-specific to the patient's needs. That is, activating a nurse call button does not specify the patient's condition. A caregiver must first enter the patient room to inquire about the patient's needs, e.g. the patient may need ice chips. Assistance to the patient would be more efficient if the caregiver was familiar with the patient's condition prior to entering the patient room.

Additionally, caregivers in the patient room may request assistance, e.g. the caregiver may need assistance administering medication. A typical call signal does not specify to the other caregivers what assistance is required. Accordingly, care for the patient can be improved by including more specific instructions to the other caregivers, e.g. the nurse's station.

Voice assistance is one technology that may be utilized to address specific needs of a patient. However, patient's need not have access to all voice commands. For example, because medications are controlled substances, a patient should not have access to a voice command to administer medication. Additionally, voice commands to control a television in the patient room may be unnecessary for a caregiver. As such, a need remains for controlled access to various voice commands in a healthcare facility.

SUMMARY

The present disclosure includes one or more of the features recited in the appended claims and/or the following features which, alone or in any combination, may comprise patentable subject matter.

According to the present disclosure, a method of providing communication in a healthcare facility may include determining with a location device whether a person is in a patient room. The method may also include activating a voice command database having a plurality of voice commands specific to the person in the patient room. The method may also include receiving one of the plurality of voice commands at an electronic device located in the patient room. The method may also include transmitting the one of the plurality of voice commands to a remote device positioned outside of the patient room.

In some embodiments, the person in the patient room may be a caregiver, and the method may include activating a voice command database includes activating a voice command database having a plurality of voice commands specific to the caregiver. The person in the patient room may be a patient, and the method may include activating a voice command database includes activating a voice command database having a plurality of voice commands specific to the patient.

If desired, the method may include monitoring vital signs of a patient in the patient room. The method may also include transmitting a warning notification to a caregiver when it is determined that a caregiver is in the patient room.

It is contemplated by this disclosure that the method may include tracking the voice command transmitted to the remote device, and generating an action item in response to the voice command. The method may also include removing the action item when a caregiver responds to the voice command. The voice command may be generated by a patient.

It is within the scope of this disclosure that the method may include tracking a location of a patient in the healthcare facility. The method may also include receiving a voice command inquiring about the location of the patient, and responding to the voice command with the location of the patient.

According to another aspect of the present disclosure, a communication system for a healthcare facility includes a locating device associated with a user. A location monitoring system may be configured to track a location of the locating device in the healthcare facility. An electronic controller may include a voice command database having a plurality of voice commands. The electronic controller may activate the voice command database when the location monitoring system determines that the user is located in a patient room. A microphone may be located in the patient room to receive one of the plurality of voice commands. The electronic controller may transmit the one of the plurality of voice commands to a remote device positioned outside of the patient room.

In some embodiments, the locating device may be worn by a caregiver and the location monitoring system may determine the location of the caregiver. The electronic controller may activate a voice command database having a plurality of voice commands associated with the caregiver when the caregiver is determined to be in the patient room. The locating device may be worn by a patient and the location monitoring system may determine the location of the patient. The electronic controller may activate a voice command database having a plurality of voice commands associated with the patient when the patient is determined to be in the patient room.

It is contemplated by this disclosure that a vital signs monitor may monitor vital signs of a patient in the patient room. A speaker may transmit a warning notification to a caregiver when it is determined that a caregiver is in the patient room.

If desired, the electronic controller may track the voice command transmitted to the remote device and generate an action item in response to the voice command. The action item may be removed when a caregiver responds to the voice command.

If desired, the remote device may be located at a nurse's station.

According to another aspect of the present disclosure, a communication system for a healthcare facility may include a real time locating system configured to track a location of a person in the healthcare facility. An electronic controller may be provided including a microphone to receive voice commands from the person in the healthcare facility. A voice command database may be provided having multiple command libraries. Each command library may be related to one of a plurality of people in the healthcare facility. The voice command database may be electronically coupled to the electronic controller to receive the voice commands from the electronic controller. A device in the healthcare facility may be electronically coupled to the voice command database. The device may be operated by the voice commands received at the voice command database.

In some embodiments, the command libraries may include a patient command library, a caregiver command library, a doctor command library, and a housekeeper command library. A locating device may be worn by the person in the healthcare facility. The locating device may be worn by a caregiver and the voice command library may be a caregiver library. The locating device may be worn by a patient and the voice command library may be a patient library. The locating device may be worn by a doctor and the voice command library may be a doctor library. The locating device may be worn by a housekeeper and the voice command library may be a housekeeper library.

It may be desired that the real time locating system determines if the person in the healthcare facility is within a predetermined distance from the device. The voice commands may operate the device if the person is within the predetermined distance from the device. The voice commands may not operate the device if the person is not within the predetermined distance from the device.

According to a further aspect of the present disclosure, a method of operating a device in a healthcare facility may include tracking a location of a person in the healthcare facility. The method may also include receiving voice commands from the person in the healthcare facility at a voice command database having multiple command libraries, wherein each command library is related to one of a plurality of people in the healthcare facility. The method may also include operating a device in the healthcare facility based on the voice commands received at the voice command database if the person in the healthcare facility is within a predetermined distance from the device.

In some embodiments, the command libraries may include a patient command library, a caregiver command library, a doctor command library, and a housekeeper command library. The voice commands may not operate the device if the person is not within the predetermined distance from the device.

It may be desired that the method also includes locating a caregiver and activating a caregiver library at the voice command database. The method may also include locating a patient and activating a patient library at the voice command database. The method may also include locating a doctor and activating a doctor library at the voice command database. The method may also include locating a housekeeper and activating a housekeeper library at the voice command database.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
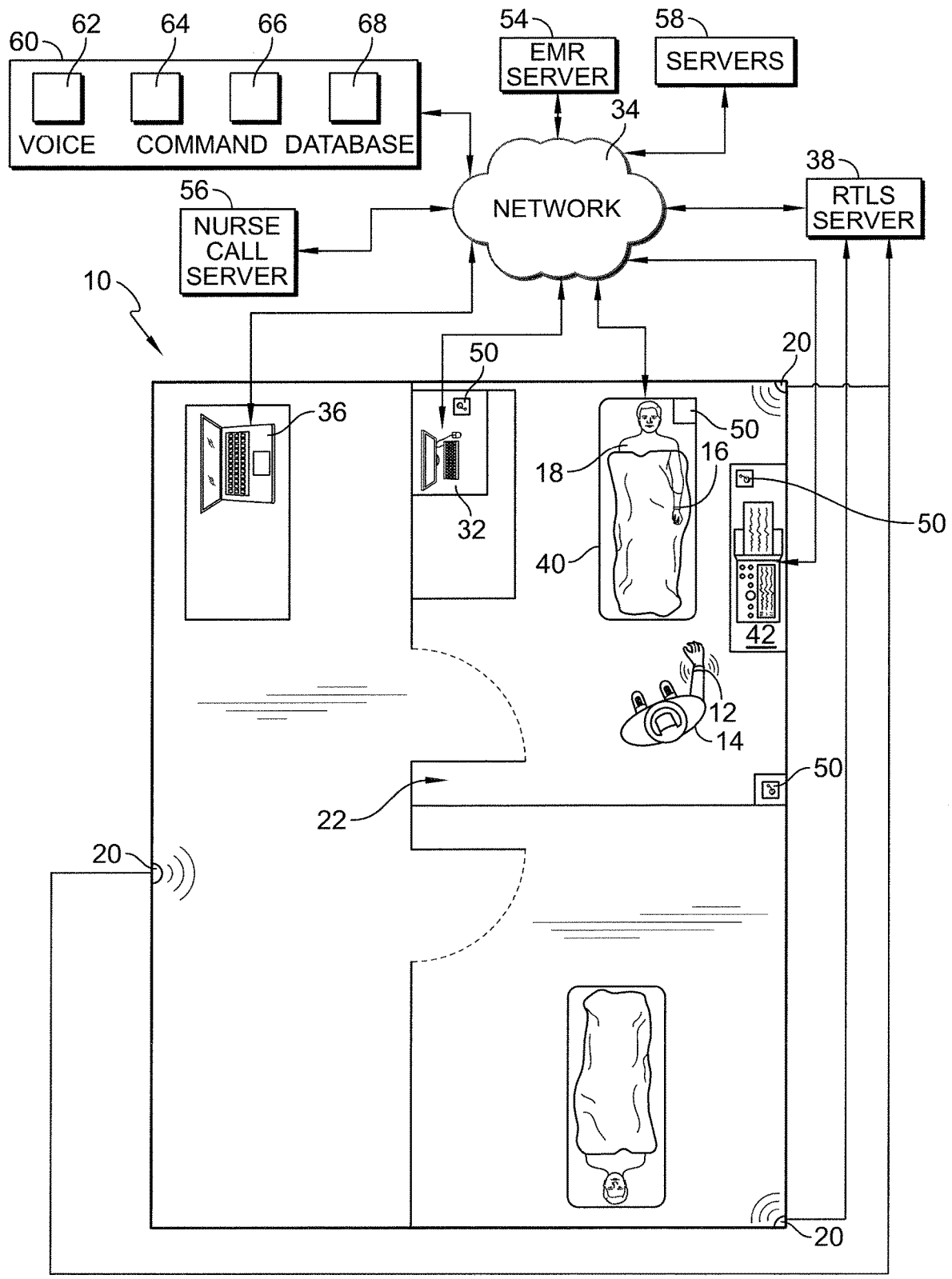
FIG. 1 is a diagrammatic top plan view of patient rooms of a healthcare facility showing a voice recognition system that receives voice commands from users within a patient room.

Referring to FIG. 1, a healthcare system 10 includes locating system 30 to track the whereabouts of caregivers and patients in a health care facility such as a hospital or nursing home includes mobile staff tags 12 worn by staff members such as caregivers 14 and mobile patient tags 16 worn by patients 18. As described in more detail below, various voice command databases are activated based on the whereabouts of patients 18 and caregivers 14. Locating system 30 has a multitude of transceivers 20 dispersed throughout patient rooms 22. System 10 includes a hub computer 36 which is communicatively coupled to other hub computers 36 of system 10 via a network 34 of the healthcare facility. In the illustrative example, system 10 is also communicatively coupled to other remote computers 32 of the healthcare facility. Such other remote computers 32 include, for example, nurse call computers, electronic medical records (EMR) computers, admission/discharge/transfer (ADT) computers, and the like. According to this disclosure, locating system 30 operates as a high-accuracy locating system which is able to determine the location of each tag 12, 16 in communication with the transceivers 20.

One example of a high-accuracy locating system contemplated by this disclosure is an ultra-wideband (UWB) locating system. UWB locating systems operate within the 3.1 gigahertz (GHz) to 10.6 GHz frequency range. Suitable transceivers 20 in this regard include WISER Mesh Antenna Nodes and suitable tags 12, 16 in this regard include Mini tracker tags, all of which are available from Wiser Systems, Inc. of Raleigh, N.C. and marketed as the WISER LOCATOR™ system.

In some embodiments, locating system 30 uses 2-way ranging, clock synchronization, and time difference of arrival (TDoA) techniques to determine the locations of tags 12, 16 in the X and Y and, optionally, Z dimensions. See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 20 and the various mobile tags 12, 16 are determined based on bidirectional wireless signals communicated between tags 12, 16 and transceivers 20. For example, the distance from each transceiver 20 to any particular tag can be resolved onto the X-Y plane as a circle having a radius equal to the distance and having its center at the particular transceiver 20. The actual location of the mobile tag 12, 16 is determined based on the point of intersection of three or more of the circles defined by radii from three or more corresponding transceivers 20.

It should be appreciated that, unless a tag 12, 16 is midway between two transceivers 20 on a straight line connecting the two transceivers 20 (in which case the two circles generated will be tangent to each other at a single point), then two circles that are generated from the two transceivers 20 will intersect at two points such that a circle generated from a third transceiver is needed to determine which of the two points is the one corresponding to the location of the tag 12, 16. Generating fourth, fifth, sixth, etc. circles having other transceivers 20 as their respective centers will further increase the accuracy of determining the actual location of the particular tag 12, 16. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 12, 16 of interest on the X-Y plane. These considerations are discussed in International Publication No. WO 2017/083353 A1 which is already incorporated by reference herein.

Tracking the locations of multiple mobile tags 12, 16 in substantially real time using 2-way ranging, clock synchronization, TDoA, resolution of circles onto the X-Y plane, and interpolating intersection point clusters of the circles requires a large amount of computational power by hub computers 36, 32 and/or the associated locating server 38. Thus, each hub computer 36, 32 receives incoming data from a predetermined number of transceivers 20. In the illustrative example of FIG. 1, hub computer 36 receives data from four transceivers 20. TDC Acquisition Holdings, Inc. of Huntsville, Ala. which does business as Time Domain, makes a hub computer (referred to as the PLUS Synchronization Distribution Panel) that is capable of receiving incoming data from up to 144 transceivers. The locating server or computer 36, in turn, receives data from the various hubs 36, 32 and tracks or monitors the locations of tags 12, 16 in the healthcare facility.

The patient room 22 includes a patient support apparatus 40. The patient support apparatus 40 is illustrated as a bed; however, the patient support apparatus 40 may take the form of any apparatus for supporting a patient, e.g. a stretcher, a chair, a wheelchair, a bench, and so forth. The patient support apparatus 40 supports a patient thereon. A vital signs monitor 42 is positioned near and/or coupled to the patient support apparatus 40. The vital signs monitor 42 monitors vital signs of the patient 18, e.g. heartrate, blood pressure, respiratory rate, or the like.

The system 10 includes electronic voice recognition devices 50 configured to receive voice commands from persons with a patient room 22. As illustrated in FIG. 1, the electronic voice recognition devices 50 may be positioned on the patient support apparatus 40, the vital signs monitor 42, or the hub computer 32. Alternatively, or in addition to, the electronic voice recognition devices 50 may be incorporated into the patient tag 16. A voice recognition device 50 may also be embedded in each staff tag 12. In some embodiments, the voice recognition device 50 may be incorporated in the graphical room stations of a nurse call system.

Each voice recognition device 50 is in communication with the network 34 and may be in communication with the real time locating system server 38, an electronic medical record server 54, a nurse call station server 56, or other servers 58. In the illustrative embodiment, a voice command server 60 includes libraries of commands, e.g. caregiver commands 62, patient commands 64, doctor commands 66, or housekeeping commands 68. The voice command server 60 may be pre-loaded with voice recognition to recognize various individual's voices. For example, a doctor or nurse, upon starting employment with the healthcare facility may have their voice recorded and linked to the respective doctor library or nurse library. Accordingly, when the doctor or nurse uses one of the respective doctor commands or nurse commands, their voice is recognized by the voice command server 60. A housekeeper may also have their voice recorded and linked to the housekeeper library. Additionally, upon admittance to the healthcare facility, a patient may have their voice recorded and linked to a patient library. In other embodiments, the patient commands in the patient library are available to anyone so that a voice is not required to be recorded.

In some embodiments, the voice command server 60 is linked to the nurse call station server 56 so that any nurse can issue voice commands to the voice command sever 60. That is, voice commands originated at the nurse call station are not required to be recognized since all commands are assumed to originate from a nurse. In some embodiments, the voice command server 60 is linked to the electronic medical record server 54 so that all medical related commands are automatically recorded in the patient's medical record. For example, if a nurse issues a command to administer medication, the electronic medical record is updated to reflect that medication was requested. When the medication is administered, the nurse can utilize the voice command server 60 to update the electronic medical record with the date, time, and dosage of medication. In some embodiments, the voice command server 60 is linked to the real time locating system server 38 to activate various voice commands. For example, a voice command to start an electrocardiogram may only be activated if a nurse or doctor is detected as being within a predetermined range, e.g. three feet, of the electrocardiogram. As another example, a voice command to control an intravenous drip may only be activated if the nurse or doctor is within a predetermined range of the intravenous drip.

In some embodiments, the voice command server 60 controls various functions within the patient's room, e.g. entertainment system, lights, window shades, and bed controls. In such an embodiment, the voice command sever 60 may not be required to recognize a voice, but rather can be activated by any voice. Additionally, some voice commands, e.g. room control commands, may be universal to the command databases. That is, some voice commands may be universal to doctors, nurses, patients, and housekeeping. Also, it may be desired to have additional voice command databases, e.g. administration database, family database, etc.

Figure 2:
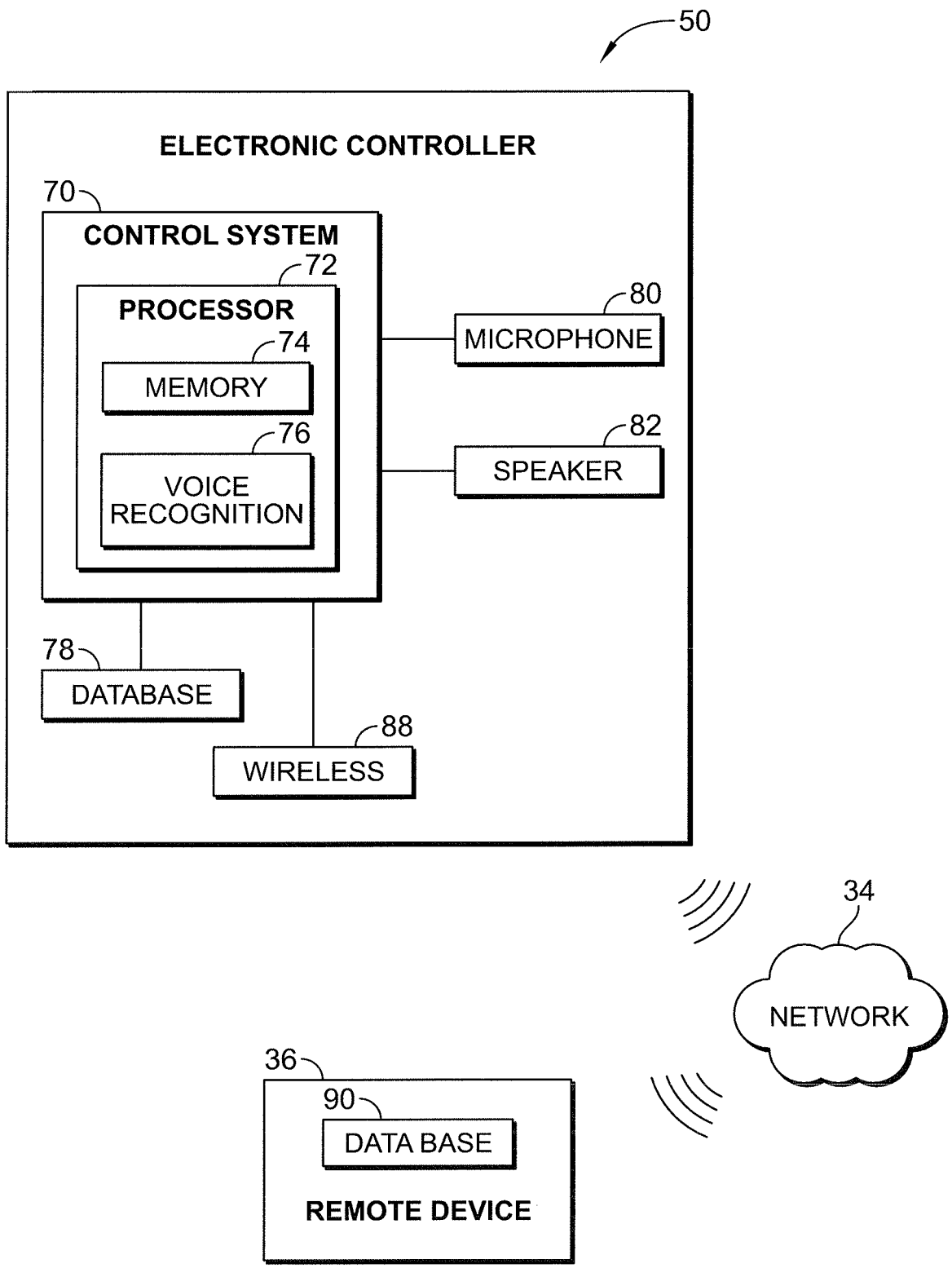
FIG. 2 is a schematic of an electronic controller having a voice command database including a plurality of voice commands.

Referring to FIG. 2, an embodiment of the electronic voice recognition device 50 illustratively includes a control system 70 having a processor 72, a memory 74, and a voice recognition module 76. The processor 72 may be embodied as any type of processor capable of performing the functions described herein. The processor 72 may be embodied as a dual-core processor, a multi-core or multi-threaded processor, digital signal processor, microcontroller, or other processor or processing/controlling circuit with multiple processor cores or other independent processing units. The memory 74 may be embodied as any type of volatile or non-volatile memory or data storage capable of performing the functions described herein. In operation, the memory 74 may store various data and software used during operation of the electronic voice recognition device 50 such as operating systems, applications, programs, libraries, and drivers. The memory 74 includes a plurality of instructions that, when read by the processor, cause the processor 72 to perform the functions described herein.

A data storage device 78 is provided that may be embodied as any type of device or devices configured for short-term or long-term storage of data such as, for example, memory devices and circuits, memory cards, hard disk drives, solid-state drives, or other data storage devices. The data storage device 78 includes a plurality of voice command databases, each having a plurality of voice commands specific to an individual in the patient room 22. A microphone 80 and speaker 82 are provided to enable communication between a user and the electronic voice recognition device 50. The microphone 80 is configured to receive voice commands from a user and send an output signal to the processor 72. Based on the output signals, the processor 72 transmits a signal over a wireless transceiver 88 indicative of the voice command. The wireless transceiver 88 may be embodied as any communication circuit, device, or collection thereof, capable of enabling wireless communications between the electronic voice recognition device 50 and the remote computers 36 over the network 34. The wireless transceiver 88 may be configured to use any one or more communication technology and associated protocols (e.g., Wi-Fi®, Bluetooth®, WiMAX, etc.) to effect such communication. Alternatively, or in addition to, the electronic voice recognition device 50 may be hardwired to the remote computers 36. In the illustrative embodiment, the remote computers 36 also include a data storage device 90 similar to the data storage device 78 and including a plurality of voice command databases, each having a plurality of voice commands specific to an individual in the patient room 22.

The data storage devices 78, 90 include a patient voice command database including a plurality of voice commands specific to the patient 18. For example, the commands may include "need ice chips," "need pain medication," "need to use the restroom," etc. Each voice command in the patient voice command database is related to a request that may be made by the patient. The data storage devices 78, 90 also include a caregiver voice command database including a plurality of voice commands specific to the caregiver 14. For example, the commands may include "administer medication," "CPR," "change bed," etc. Other voice command databases may be contemplated. For example, a housekeeper voice command database may be provided that is specific to a housekeeper. In some embodiments, separate voice command databases may be provided for doctors and nurses. In some embodiments, a voice command database may be provided that is specific to family members in the patient room 22.

Although FIG. 2 illustrates both data storage devices 78, 90, the system 10 may operate with only the data storage device 78. That is, the processor 72, in response to the output signal from the microphone 80, is instructed to relate the output signal to a voice command in the data storage device 78 and transmit a signal to the remote computer 36 indicative of the voice command. In some embodiments, the system 10 may operate with only the data storage device 90. That is, the processor 72, in response to the output signal from the microphone 80, transmits the output signal to the remote computer 36. At the remote computer 36, a processor (not shown) of the remote computer 36 relates the output signal to a voice command in the data storage device 90. The remote computer 36 then activates a graphic or audible alert indicative of the voice command.

Because the patient voice commands and the caregiver voice commands are specific to the patient and the caregiver, respectively, the processor 72 is only instructed to act on a voice command when a specific voice command database is activated by the system 10. For example, if the transceivers 20 locate the patient tag 16 in the patient room 22, the patient voice command database becomes activated. If the patient 18 is not in the patient room 22, the patient voice command database is deactivated to avoid false alerts to the caregivers 14. Likewise, if a caregiver 14 is in a patient room 22, the caregiver voice command database is activated. However, if the caregiver 14 is not in the patient room 22, the caregiver voice command database is deactivated to avoid false alerts, e.g. improper administration of medication.

Figure 3:
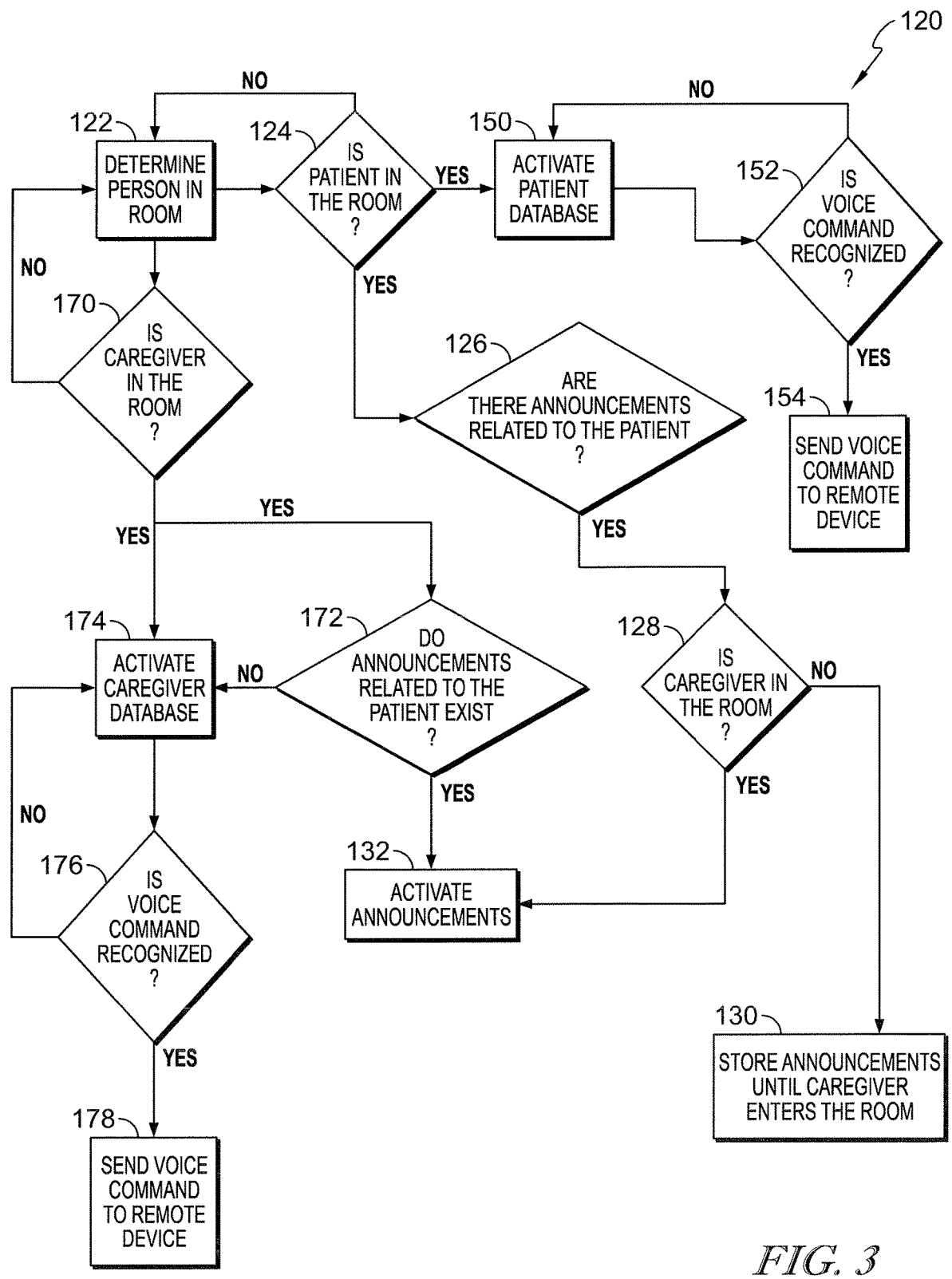
FIG. 3 is a flowchart of a routine for operating the voice command database.

Referring to FIG. 3 a routine 120 is provided for activating voice commands in the patient room 22. At block 122 the locating system 30 determines whether a person is in the patient room 22 by transmitting signals from the transceivers 20 throughout the patient room 22. At block 124, the transceivers 20 scan for return signals from the mobile patient tags 16 to determine whether a patient 18 is in the patient room 22. If the transceivers 20 do not receive a return signal from a mobile patient tag 16, the system 10 continues to transmit signals throughout the patient room 22, at block 122. If the locating system 30 determines that a patient 18 is present in the patient room 22, the system 10 determines whether any announcements exist that are related to the patient 18, at block 126. The vital signs monitor 42 is consulted to provide a summary of the patient's condition. By way of example, if the patient's blood pressure is high, an announcement is prepared to alert the caregiver 14 of the patient's blood pressure. In another example, the system 10 may determine through various sensors that the patient 18 is at risk for developing pressure ulcers. In such a scenario, an announcement is prepared to alert the caregiver 14 to turn the patient. In yet another example, the patient 18 may have requested ice chips. The system 10 prepares an announcement to alert the caregiver 14 that ice chips have been requested.

If announcements related to the patient exist, the system 10 determines whether a caregiver 14 is in the patient room 22. At block 128, the transceivers 20 scan for return signals from the mobile staff tags 12 to determine whether a caregiver 14 is in the patient room 22. If the transceivers 20 do not receive a return signal from the mobile staff tags 12, the system 10 stores the announcements related to the patient until a caregiver 14 enters the patient room 22, at block 130. If the transceivers 20 receive a return signal from the mobile staff tag 12, indicating that a caregiver 14 is in the patient room 22, the system 10 activates the announcements, at block 132. For example, the announcements may be displayed on a screen of the hub computer 32. Alternatively, or in addition to, the speaker 82 may audibly alert the caregiver 14 of the announcements. In some embodiments, the announcements may be stored as action items on the hub computer 32 or remote computer 36. As the caregiver 14 attends to the announcements, the action items are cleared. For example, if the system 10 alerts the caregiver 14 that the patient 18 needs to be turned, upon turning the patient 18, the caregiver 14 can clear the action item. A date and time may be stamped at the hub computer 32 or the remote computer 36 indicating when the patient 18 was turned.

When the system 10 determines that a patient 18 is in the patient room 22, the system 10 also activates, at block 150, the patient voice command database stored in at least one of data storage devices 78, 90. By activating the patient voice command database, the patient 18 is permitted to use voice commands within the patient room 22. For example, the patient 18 may say, "turn on television." The processor 72 of the electronic voice recognition device 50 receives output signals from the microphone 80 indicative of the voice command. Based on the output signal from the microphone 80, the processor 72 determines whether the voice command recognized as a voice command in the patient voice command database, at block 152. If the voice command is not recognized, no action is taken. If the voice command is recognized, the processor 72 sends an output signal to the television, instructing the television to turn on.

In another example, the patient 18 may say, "need pain medication." If the processor 72 recognizes this command, the processor 72 sends an output signal to the remote computer 36, at block 154. The remote computer 36 receives the output signal and alerts the caregiver 14 of the patient request. For example, the remote computer 36 may provide a visual or audible alert to the caregiver 14. Alternatively, or in addition to, the caregiver 14 may receive an alert through the mobile staff tag 12. The caregiver 14 is instructed to administer medication to the patient 18. In some embodiments, the instructions to administer medication may be stored as action items at the remote computer 36, the hub computer 32, or the mobile staff tag 12. When the caregiver 14 attends to the patient's medication, the caregiver 14 can clear the action item. In some embodiments, a date and time stamp is recorded when the action item is cleared.

At block 170, the transceivers 20 scan for output signals from a mobile staff tag 12 to determine whether a caregiver 14 is in the patient room 22. If a caregiver 14 is not in the patient room 22, the system 10 continues to monitor for people in the patient room 22, at block 122. If an output signal is received by one of the transceivers 20 in the patient room 22, the system determines that a caregiver 14 has entered the patient room 22. If a caregiver 14 is in the patient room 22, the processor 72 determines whether any announcements are stored for the caregiver, at block 172. If an announcement is present, the system 10 notifies the caregiver 14, at block 132. For example, if the patient 18 requires turning the caregiver 14 is alerted to turn the patient 18. The caregiver 14 may be alerted audibly through the speaker 82. Alternatively, or in addition to, an action item may be populated in the hub computer 32. After the caregiver 14 attends to the patient, the caregiver 14 clears the action item indicating that the patient has been turned. A date and time stamp may be recorded to document when the patient was turned.

At block 174, the processor 72 activates the caregiver voice command database. By activating the caregiver voice command database, caregiver specific voice commands become operable. It may be desired that certain caregiver voice commands are only operable when the caregiver 14 is present in the patient room 22. For example, the caregiver 14 may say, "administer pain medication." The microphone 80 sends an output signal to the processor 72 indicative of this command. At block 176, the processor 72 determines whether the command is recognized. If the command is recognized, the processor 72, at block 178, sends an output signal to the remote computer 36 indicating that pain medication is required. A caregiver 14 at the remote computer 36 is then able to prepare the pain medication for administration. Because, the command is only activated when the caregiver 14 is in the patient room 22, the patient 18 is not capable of receiving pain medication without the caregiver's knowledge. In another example, the caregiver 14 may say, "administer CPR." Upon receiving this command at the remote computer 36, other caregivers 14 are alerted that CPR is required in the patient room 22.

It should be noted that the voice commands may be recorded at one of the hub computer 32 or the remote computer 36. That is, a log may be kept of all voice commands received by the system 10. The log may include both patient specific and caregiver specific voice commands. Additionally, the voice command database may include other specific voice commands. For example, the system 10 may include a housekeeping voice command database, a maintenance voice command database, or a family voice command database. The family voice command database may allow family members present in the patient room 22 to receive updates on the patient's condition. For example, if the patient 18 is not currently in the patient room 22, the family may be alerted as to the patient's location. In some embodiments, a family member may ask where the patient is. The family voice command database detects this inquiry and the system responds by identifying the location of the patient. Because each of these voice command databases are specific to an individual and only operable when that person is in the patient room, other persons are prohibited from utilizing commands that are not specific to them. Such isolation of the voice command databases facilitates preventing misuse of the various voice commands.

Figure 4:
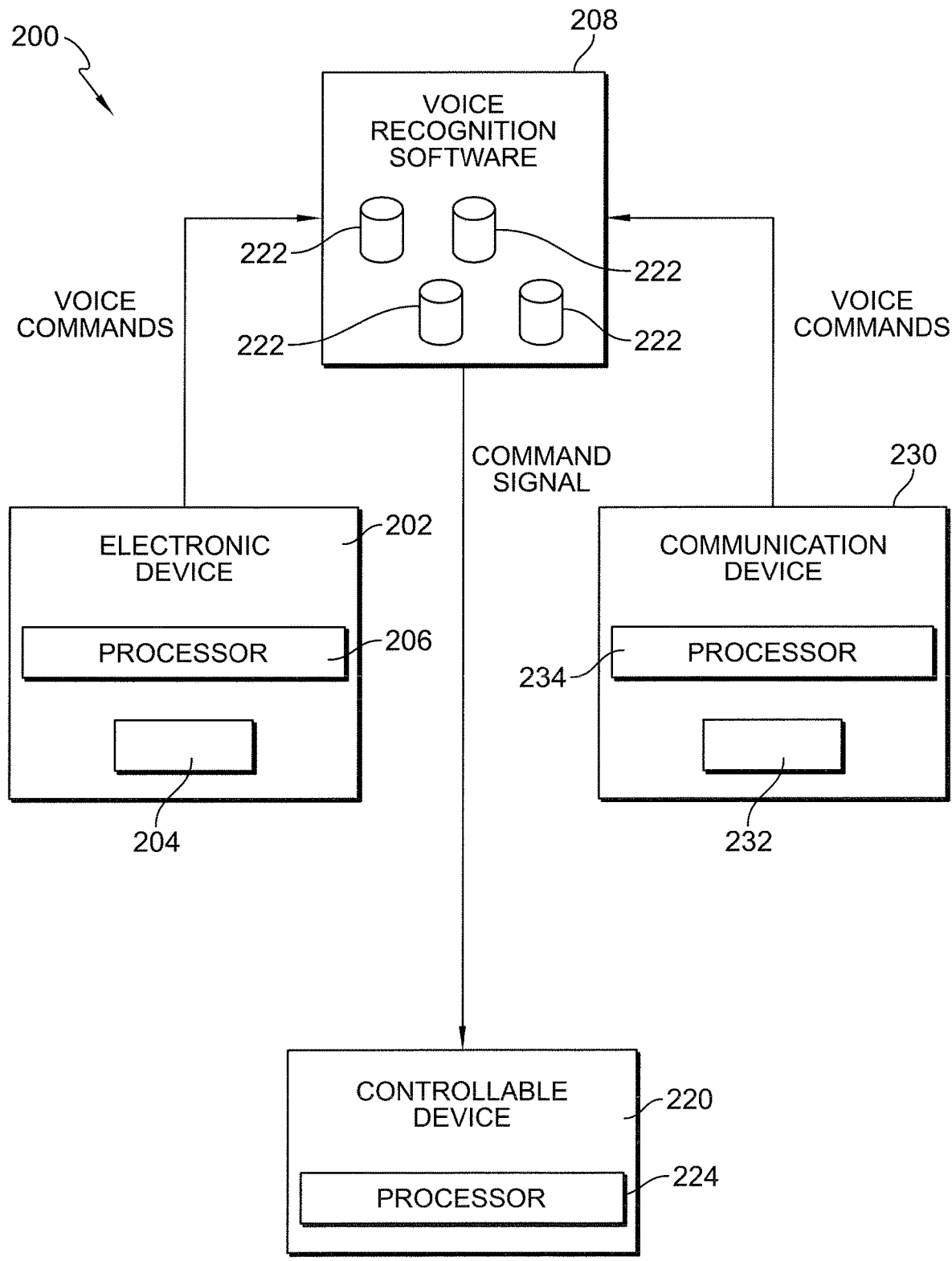
FIG. 4 is a schematic of another embodiment of a healthcare management system that may be used independently of the system shown in FIG. 1 or in combination with the system shown in FIG. 1.

FIG. 4 illustrates another embodiment of a healthcare management system 200 having an electronic voice recognition device 202. The electronic voice recognition device 202 may be positioned on the patient support 40. In another embodiment, the electronic voice recognition device 202 is a pillow speaker at the patient support 40. In some embodiments, the electronic voice recognition device 202 is positioned at a nurses call station. The electronic voice recognition device 202 includes a microphone 204 configured to receive voice commands. Control circuitry 206 converts the voice commands into voice packets and transmits the voice packets to voice recognition software 208. In some embodiments, the control circuitry 206 only transmits the voice packets if the electronic voice recognition device 202 is within a predetermined distance from a controllable device 220.

A remote device 230 is also in communication with the voice recognition software 208. The remote device 230 includes a microphone 232 to receive voice commands. In some embodiments, the remote device 230 is a phone, a tablet, or an audio station that may be operated by a caregiver or doctor when caring for a patient. In some embodiments, the remote device 230 is a patient device. The remote device 230 is configured to receive voice commands from a user, e.g. caregiver, doctor, patient. The voice commands are converted to voice packets by a control circuitry 234 of the remote device 230 and transmitted to the voice recognition software 208.

The voice recognition software 208 includes a plurality of voice command libraries 222. For example, the voice command libraries 222 may include a patient library that is related to a patient electronic voice recognition device 202. The voice command libraries 222 may include a caregiver library that is related to a caregiver voice recognition device 202. The voice command libraries 222 may include a doctor library that is related to a doctor voice recognition device 202. The voice command libraries 222 may include a housekeeper library that is related to a housekeeper voice recognition device 202. The voice recognition software 208 is configured to recognize the voice of the individual providing a voice command to the electronic voice recognition device 202 and determine which voice command library is related to the voice command.

The voice recognition software 208 determines which controllable device 220 is related to the voice command and converts the voice command into a control signal that is transmitted to the controllable device 220, which includes control circuitry 224 to read the control signal. In some embodiments, the controllable device 220 may include the patient support 40. Accordingly, the patient or caregiver may voice a command to the electronic controller 220, e.g. "raise bed." This command is delivered to the voice recognition software, which, in turn, sends a control signal to the patient support 40 to raise the bed. Other commands related to the patient support 40 may be contemplated. In some embodiments, the controllable device 220 may be a patient intravenous drip. In such an embodiment, the caregiver or doctor may voice a command, e.g. "start IV," which is transmitted to the voice recognition software 208. The voice recognition software 208 then sends a command signal to the intravenous drip to start the IV. Other commands related to the intravenous drip may also be contemplated. In some embodiments, the controllable device 220 may include an electrocardiogram. Accordingly, the caregiver or doctor may voice a command, e.g. "start EKG," which is transmitted as a voice packet to the voice recognition software 208. The voice recognition software 208 then transmits a command signal to the electrocardiogram to start the electrocardiogram. In another embodiment, the controllable device 220 may be a room feature the patient room, e.g. window blinds or lighting. Accordingly, the patient, the doctor, the caregiver, or a housekeeper may voice a command, e.g. "open blinds," "close blinds," "dim lights," "turn on lights," etc. The voice command is then sent to the voice recognition software 208 as a voice packet that is converted to a command signal to control the controllable device 220. It should be appreciated that the voice command software 208 may be capable of receiving voice commands and sending command signals related to any device in the patient room. For example, the voice commands may be used to operate the entertainment features of the patient room, e.g. television, radio, etc., or other medical apparatuses within the room, e.g. ventilator, oximeter, etc.

In some embodiments, the voice recognition software 208 converts the voice packet to a command displayed at the nurse's station or other remote device 36. For example, the doctor may voice a command, e.g. "increase [medication] to [dosage]" or "will need medication in five minutes." The voice recognition software 208 then sends a control signal to the nurse's station to display the medication type and dosage. Accordingly, caregivers and doctors can communicate through the voice recognition software 208 by sending voice commands that are displayed from other caregivers and/or doctors. In one embodiment, caregivers and/or doctors can communicate through the voice recognition software. For example, the caregiver and/or doctor may voice a command, e.g. "medication administered at [time]" or "patient on side for 30 minutes." The other caregivers and doctors may then be alerted through the voice recognition software 208. In some embodiments, the voice recognition software 208 sends command signals to an electronic medical record that is updated based on the voice command.

In some embodiments, the electronic voice recognition device 202 is a pillow speaker that monitors the sleep patterns of the patient. For example, the pillow speaker monitors for abnormal breathing and/or snoring. If such abnormal breathing or snoring is detected, the electronic voice recognition device 202 sends a control signal to the nurse's station indicating that the patient requires attention, e.g. the patient needs to be turned. In some embodiments, vital signs are also monitored to determine whether the patient requires attention. The voice recognition device 202 may also record sounds from the patient. The sounds may be parsed for voice recognition to determine patient satisfaction. That is, the voice recognition device 202 may monitor for keywords from the patient to determine whether the patient is comfortable. For example, patient complaints while the patient is in the patient room may be recorded and delivered to a nurse's station to notify the nurse that the patient is not satisfied with their care.

Figure 5:
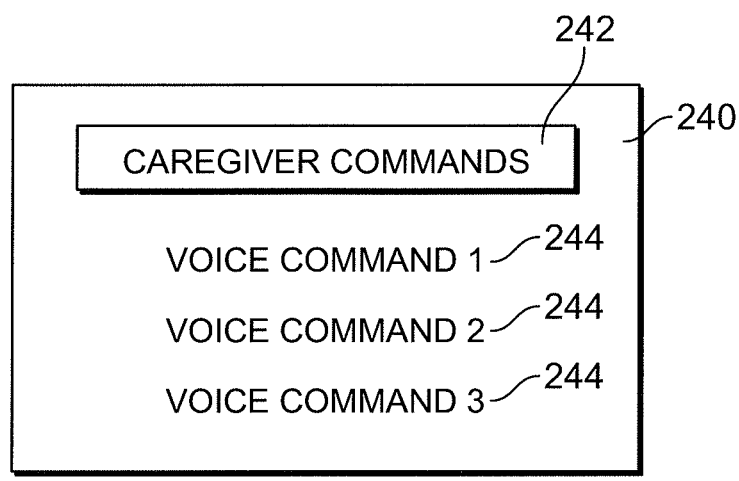
FIG. 5 is a screen shot of a graphical user interface in accordance with an embodiment.

Referring to FIG. 5 a screen 240 may be displayed on the computers 32, 36 and/or on the remote device 230. The screen 240 includes lists of voice commands that are available. For example, by selecting a caregiver list 242, a plurality of voice commands 244 available to the caregiver is displayed. Other lists that may be displayed include a doctor list, a patient list, a housekeeper list, etc. The lists may be displayed automatically in response to the respective caregiver being detected in the room by locating system 30 or detected within a threshold proximity (e.g. 3 feet) of the computer 32, 36 or device 230. Displaying lists of voice commands that are available to the caregiver(s) in the room is helpful if there are many available voice commands because caregivers may not remember all of them otherwise.

Although this disclosure refers to specific embodiments, it will be understood by those skilled in the art that various changes in form and detail may be made without departing from the subject matter set forth in the accompanying claims.

The invention claimed is:

1. A communication system for a healthcare facility comprising:
    a real time locating system configured to track a location of one of a plurality of people in the healthcare facility,
    an electronic controller including a microphone to receive voice commands from the person in the healthcare facility,
    a voice command database having multiple command libraries, each command library including a plurality of voice commands specific to one of the plurality of people in a room, the voice command database electronically coupled to the electronic controller to receive one of the plurality of voice commands from the electronic controller,
    a device in the healthcare facility that is electronically coupled to the voice command database, the device operated by the one of the plurality of voice commands received at the voice command database.

2. The communication system of claim 1, wherein the command libraries include a patient command library, a caregiver command library, a doctor command library, and a housekeeper command library.

3. The communication system of claim 1, wherein the real time locating system determines if the person in the healthcare facility is within a predetermined distance from the device, the one of the plurality of voice commands operating the device if the person is within the predetermined distance from the device.

4. The communication system of claim 3, wherein the one of the plurality of voice commands does not operate the device if the person is not within the predetermined distance from the device.

5. The communication system of claim 1, further comprising a locating device worn by the person in the healthcare facility.

6. The communication system of claim 5, wherein the locating device is worn by a caregiver and the voice command library is a caregiver library.

7. The communication system of claim 5, wherein the locating device is worn by a patient and the voice command library is a patient library.

8. The communication system of claim 5, wherein the locating device is worn by a doctor and the voice command library is a doctor library.

9. The communication system of claim 5, wherein the locating device is worn by a housekeeper and the voice command library is a housekeeper library.

10. A method of operating a device in a healthcare facility comprising:
tracking a location of one of a plurality of people in the healthcare facility,
receiving voice commands from the person in the healthcare facility at a voice command database having multiple command libraries, each command library including a plurality of voice commands specific to one of the plurality of people in a room,
operating a device in the healthcare facility based on one of the plurality of voice commands received at the voice command database if the person in the healthcare facility is within a predetermined distance from the device.

11. The method of claim 10, wherein the command libraries include a patient command library, a caregiver command library, a doctor command library, and a housekeeper command library.

12. The method claim 10, wherein the one of the plurality of voice commands does not operate the device if the person is not within the predetermined distance from the device.

13. The method of claim 10, further comprising locating a caregiver and activating a caregiver library at the voice command database.

14. The method of claim 10, further comprising locating a patient and activating a patient library at the voice command database.

15. The method of claim 10, further comprising locating a doctor and activating a doctor library at the voice command database.

16. The method of claim 10, further comprising locating a housekeeper and activating a housekeeper library at the voice command database.

\* \* \* \* \*